United States Patent [19]
Jay

[11] Patent Number: 4,761,843
[45] Date of Patent: * Aug. 9, 1988

[54] HEMORRHOID SEAT CUSHION

[75] Inventor: Eric C. Jay, Boulder, Colo.

[73] Assignee: Jay Medical, Ltd., Boulder, Colo.

[*] Notice: The portion of the term of this patent subsequent to Apr. 28, 2004 has been disclaimed.

[21] Appl. No.: 42,172

[22] Filed: Apr. 24, 1987

Related U.S. Application Data

[63] Continuation-in-part of Ser. No. 736,291, May 20, 1985, Pat. No. 4,660,238.

[51] Int. Cl.$^4$ .................. A61F 5/34; A47C 27/08; A61G 7/04
[52] U.S. Cl. ........................... 5/431; 128/78; 128/98.1
[58] Field of Search ............... 5/451, 450, 481, 431, 5/441, 448, 449; 128/78, 98.1, 68, 168; 297/DIG. 1

[56] References Cited

U.S. PATENT DOCUMENTS

| | | | |
|---|---|---|---|
| 717,659 | 1/1903 | Clark | 128/98.1 |
| 2,249,298 | 7/1941 | Ratti | 128/98.1 |
| 2,615,445 | 10/1952 | Holmes | 128/98.1 |
| 3,308,491 | 3/1967 | Spence | 5/450 |
| 3,611,455 | 10/1971 | Gottfried | 5/451 |
| 3,721,232 | 3/1973 | Trenchard | 128/68 |
| 4,709,431 | 12/1987 | Shaktman | 5/431 |

*Primary Examiner*—Alexander Grosz
*Attorney, Agent, or Firm*—Donald E. Egan

[57] ABSTRACT

A hemorrhoid supporting pad assembly comprises a pad on a supporting surface which may be a seat cushion assembly. The pad is formed from a flexible envelope partially filled with a fluid. The pad is positioned on the supporting surface beneath a seated person. Lateral portions of the envelope containing the fluid extend beneath the seated person. The weight of the seated person causes the fluid in the lateral portions of the envelope to flow toward the central region of the envelope, where the fluid is forced upwardly, beneath the anus, to support the hemorrhoid.

8 Claims, 1 Drawing Sheet

HEMORRHOID SEAT CUSHION

BACKGROUND OF THE INVENTION

This is a continuation-in-part of application Ser. No. 736,291 filed May 20, 1985 now U.S. Pat. No. 4,660,238.

This invention relates in general to a hemorrhoid supporting assembly for a human body. More particularly, this invention is directed to a comfortable supporting seat cushion assembly that is specifically designed to alleviate discomfort and pain associated with hemorrhoids and similar afflictions. The present invention also relates to a pad which may be used by a hemorrhoid sufferer on any seating support without the need for a specially designed cushion assembly.

It has long been recognized that hemorrhoids are overly stretched varicose veins in the region around the anus. Swollen hemorrhoidal veins are comparable to varicose veins in the legs.

Hemorrhoids are very common—up to half of all adult Americans have hemorrhoids at one time or another. Often the hemorrhoids cause little or no discomfort and go unnoticed. Frequently, heavy internal pressure caused by heavy lifting, sitting, pregnancy and other factors causes the hemorrhoids to swell and become very painful. Increase in pressure can cause hemorrhoids to rupture which result in the passage of blood during a bowel movement.

Gravity imposes constant pressure on the delicate veins that surround the rectal area. While most veins in the body have valves to prevent the back-flow of blood and keep it moving toward the heart, there are no such valves in most lower rectal veins. Therefore, when a person sits or stands upright, the entire weight and blood pressure of the abdomen bears on the tiny vessels in the lower end of the intestine, the rectum. When additional pressure brought on by lifting or the like causes excessive resistance to flow in the rectal area, the smaller veins begin to stretch and stretch, like tiny balloons. Sometimes they lose their elastic property and become engorged with blood, gradually forming hemorrhoids over a period of time. When the hemorrhoids are formed, bleeding often follows and a painful situation ensues.

Hemorrhoid pain is most frequently encountered in the sitting position. While standing, a person's buttocks tend to be close together, thus providing some support to the hemorrhoids. However, when a person is seated, the buttocks spread apart, thus removing all support for the hemorrhoid. Thus many people who make their living while seated are afflicted by hemorrhoid pain. Particularly, those who are subjected to vibration while seated, such as truck drivers and heavy equipment operators, in addition to having no support for their hemorrhoids, may experience abrasion of the hemorrhoids caused by the vibration of their vehicles.

In the past, hemorrhoids have been treated by a variety of techniques, some of which include surgery and/or medication. Several different styles of surgery have been employed, including cryosurgery which, in essence, freezes the hemorrhoid; ligation—wherein a rubber band is used to cut off the blood supply to the hemorrhoid and literally choke it; and conventional excision involving hospitalization and anthesia. During the recovery from such surgery, patients are frequently provided with a donut shaped ring to sit on, which was thought to be helpful in order to prevent pressure on hemorrhoids or the blood vessels adjoining the area adjacent to the point of excision of the hemorrhoids. The donut shaped rings provide no support for the hemorrhoids and, consequently, do not ease the pain of the hemorrhoids or the pain following surgery.

SUMMARY OF THE INVENTION

The present invention provides a pad which may be associated with a seat cushion assembly which provides support for the hemorrhoid, or the hemorrhoid area, by providing a compensating, upward supporting pressure for the hemorrhoid area. It has been found that the application of upward supporting fluid pressure to the hemorrhoid area, provided by the present invention, significantly reduces the pain and discomfort associated with hemorrhoids and at times will promote the natural process by which hemorrhoids heal and shrink.

The present invention provides a hemorrhoid supporting assembly which is based upon a pad or pouch partially filled with a flowable fluid. The pad or pouch is positioned on a supporting surface adapted to support the pad or pouch as well as the weight of a seated person.

In the illustrated embodiment, the pad or pouch is supported upon a contoured support layer of firm, resilient foam designed to provide an even distribution of seating pressure across the gluteal region of the seated person. In this embodiment, the pad or pouch may be positioned in an opening provided in the contoured support layer in the area beneath the anus. Alternatively, the pad or pouch may be supported on a firm supporting surface, such as a wooden chair, which also supports the seated person.

It is deemed essential that the pad or pouch be at least as wide as the area beneath the anus, have sufficient volume to fill the space beneath the anus of a seated person, and be sufficiently flexible to conform to that space and provide uniform supporting pressure throughout the area of the hemorrhoids. It is preferred that the pad or pouch be wide enough to extend at least partially under the gluteal region of a seated person, whereby the pressure generated by the weight of the seated person, in combination with the supporting surface, causes the fluid within the pad or pouch to flow toward the central region of the pad or pouch, where it is forced upwardly beneath the anus. The upward flow of the fluid beneath the anus creates an upward, hemorrhoid supporting pressure, which eases hemorrhoid pain and discomfort, but avoids abrasion of the hemorrhoid.

DETAILED DESCRIPTION OF THE INVENTION

Figure 1:
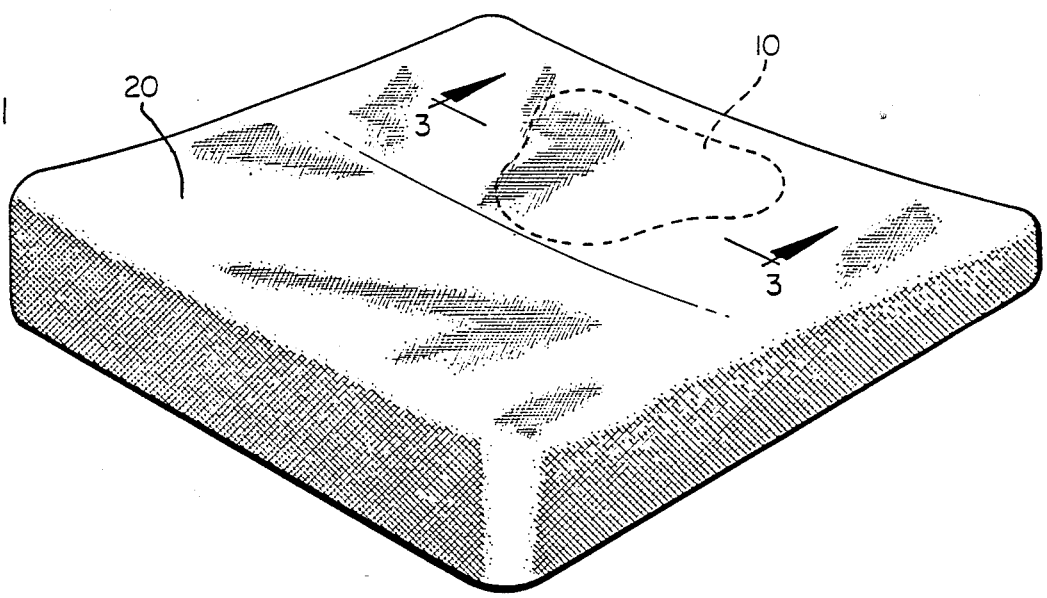
FIG. 1 is a perspective view of a cushion showing the hemorrhoid pad, in dotted lines, installed in the cushion.

In the drawings, the preferred embodiment of the present invention is illustrated, that is the hemorrhoid pad 10 is mounted in a cushion structure 20, but the hemorrhoid pad may be used on any seating surface or may be installed in items of clothing so that it assumes the desired position when the person is seated.

Figure 2:
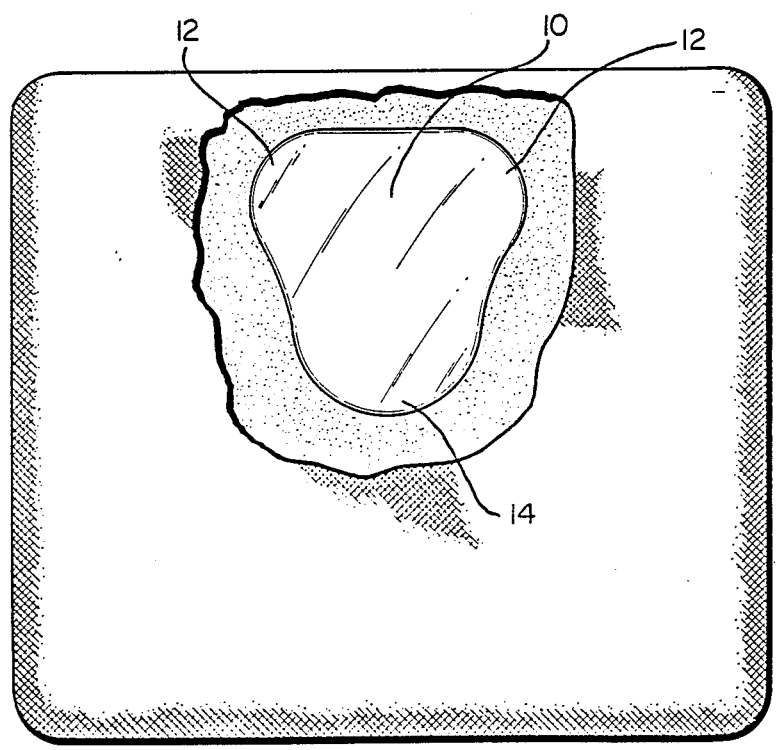
FIG. 2 is a top view of a cushion, with the upper covering cut away, showing the hemorrhoid pad of the present invention installed in a cushion.

In the embodiment shown in FIG. 2, the hemorrhoid pad is generally bell-shaped and is symmetrical about the longitudinal axis with lateral portions 12 preferably broad enough to extend beyond the area of the anus. The pad may vary from 1 or 2 inches to as much as 12 inches or more in width, but in the illustrated embodiment the preferred width is from about 5 to 7 inches. The length, including forward extension 14, is not critical and may be, for example, between 2 and 12 inches. In the preferred embodiment, forward extension 14, in combination with side portions 12, allows for some movement of the user.

Figure 3:
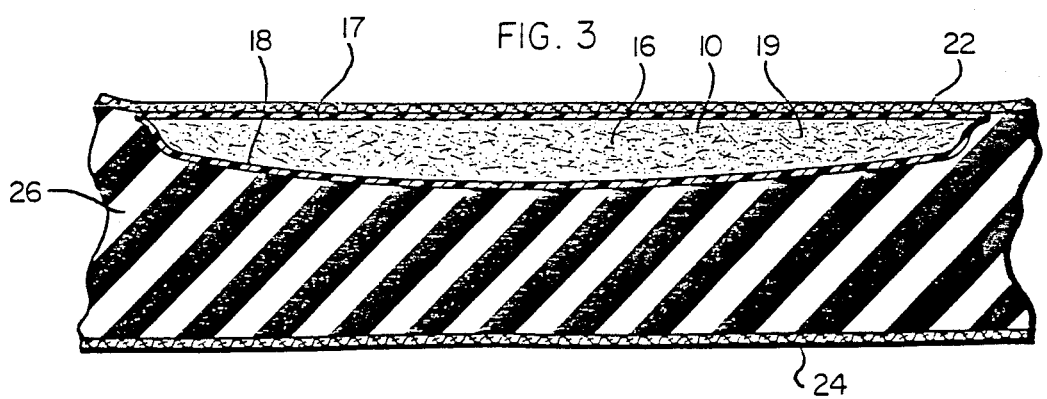
FIG. 3 is a side view taken at Section 3—3 of the cushion showing the hemorrhoid pad installed therein.

As can be seen in FIG. 3, the hemorrhoid pad 10 comprises an envelope 16 made up of flexible upper layer 17 and lower layer 18 which are sealed together about the periphery in order to provide a fluid tight seal to retain flowable fluid 19 which partially fills envelope 16.

Generally, the fluid 19 may be any fluid which does not attack or react with the upper layer 17 and the lower layer 18 of envelope 16. Sufficient fluid should be in the envelope to partially fill the envelope so that when a person is seated on the pad, at least some of the weight of the person bears upon the fluid located in the lateral portions 12 of pad 10. This causes the fluid 19 within the lateral portions 12 to flow toward the center of the pad. Because the pad is supported from beneath by the supporting surface, the fluid flows upwardly, causing the upper layer 17 of the hemorrhoid pad to move upwardly toward the anus and into the area of the hemorrhoid. The upward flow of the fluid requires that the upper layer 17 to be flexible and to have sufficient slack or be sufficiently elastomeric to allow the flowable fluid 19 to flow upwardly and support the hemorrhoid area.

In the illustrated embodiment, the hemorrhoid pad is installed in a cushion. Preferably a cover 22 surrounds the entire structure for asthetical purposes. The hemorrhoid pad may be installed in a molded cushion of the type described and claimed in co-pending application Ser. No. 614,958 and filed May 29, 1984, wherein the cushion comprises a molded layer of foam 26 which may be disposed upon base 24.

Alternatively, the hemorrhoid pad 10 may be used on any seating area, but it is most effectively used on a seating area which provides relatively firm support beneath most of the pad.

In the preferred embodiment, the hemorrhoid pad of the present invention is constructed so that lateral portions 12 extend outwardly, beyond the anal area, under the seated person. The weight of the person bears the lateral portions of the pad and the fluid in the lateral portions of the pad. This causes the flowable fluid 19 to flow away from the area of pressure (lateral portions 12) and toward the central portion of pad 10 where the combination of the pressure and the supporting member forces the flowable fluid to flow upwardly and to provide support for the hemorrhoid or the hemorrhoid area.

Pad 10 comprises an envelope 16 which may be constructed of two layers of flexible films 17 and 18, which envelope 16 is adapted to contain fluid filling material 19. Envelope 16 may be manufactured by heat sealing flexible films 17 and 18 at the edges to contain the fluid 19 material therein, as is shown in FIG. 3. In the preferred embodiment the upper film 17 is fabricated from an extensible, elastomeric material, such as a thermoplastic polyurethane. The lower film need not be flexible and may be relatively inflexible in order to provide a "built-in" supporting surface for the pad.

The Envelope

It is essential that the envelope be constructed of flexible film. It is important that the upper layer of film be pliable and impervious to the fluid retained within the envelope. Materials which are easy to heat seal and otherwise fabricate are generally preferred. Good results have been achieved using polyurethanes which are commercially available.

The envelope 16 is adapted to contain the fluid filling material 19, and depending upon the nature of the fluid used, variations may be necessary to the composition or structure of the envelope. In the preferred embodiment wherein preferred FLOLITE brand of fluid is used, the envelope may be made of flexible sheets of thermoplastic film. It is essential that the envelope be flexible at ambient room temperatures and at temperatures of use. Desirably the envelope may be made of films of thermoplastic materials, such as thermoplastic polyurethane films.

In the preferred embodiment, it is essential that the upper film used as the envelope be an extensible elastomer so that it is readily stretchable under fairly light pressure, in order to allow total conformity and encourage the upward flow of the fluid without interference of the envelope described above. It is generally preferred to use a thermoplastic material having a 100% modulus no higher than about 1,500 psi with a tensile strength at break of at least 4,500 pounds. It has been found that envelopes produced from such materials in films of 5 to 15 mils thickness produced highly desirable, stretchable envelopes which avoid or minimize the stiffness, but which are strong enough to prevent accidental punctures. It is also sometimes desirable to use two layers of film to from the upper surface of the envelope. This provides for increased flexibility, increased strength and resistance to puncturing.

The envelopes used to produce the pads of the present invention are preferably heat sealed at the edges, and are adapted to retain the fluid filling material within a defined environment. It has been found that suitable thermoplastic polyurethane films have a thickness of about 0.004 to 0.015 inch and Durometer hardness (Share A Scale) of 90 or lower, and include products such as PS 3100 series polyurethane film sold by Deerfield Urethane of South Deerfield, Maine, which has a typical tensile strength of 7,500 psi, a typical 100% modulus of 600 psi, and a typical elongation at break of 650%. Also usable, but less preferred, are "Hi-Tuff" MP-1880 or MP-1885 films supplied by Stevens Elastomeric & Plastic Products, Inc., a subsidiary of J. P. Stevens & Co., Inc., Easthampton, Mass., which MP-1800 product is a film having a typical tensile strength at 300% stretch of 2,580 psi., typical tensile strength at break (ultimate) of 7,251 psi, typical elongation at break of 440%, typical elongation set of 14.2%, and typical tear strength (Die C) of 351 psi., whereas said MP-1885 product is a film having a typical strength at 300% stretch of 1,800–2,000 psi., typical elongation at break of 500–600%, typical elongation set of 10–15%, typical tear strength (Die C) of 400–500 psi., and typical tensile strength at break (ultimate) of 6,000–7,000 psi., or a polyester-based thermoplastic polyurethane film known as "Tuftane" TF-310, sold by B. F. Goodrich General Products Company, Akron, Ohio. The two sheets of film 17 and 18 are connected by being securely heat-sealed together so as to seal and retain in place the fluid material 19 within the envelope enclosure formed between the sheets. The upper and lower films 17 and 18 may each be made up of plural layers of thermoplastic films or other materials, in order to improve strength, or heat-sealing or the like.

In the preferred embodiment, at least the upper flexible film 17 is an extensible elastomer, e.g., it is produced from a polyurethane material having a 100% modulus of no greater than about 1,500 psi. Films having a tensile strength of at least 4,500 psi are strong enough to avoid accidental tears and punctures.

If desired, one may choose to first heat-seal the envelope for the fluid filling material, but leave a small vent opening and/or a small filling port (not shown), so that a predetermined amount or volume of fluid material (the fluid may be advantageously heated prior to injection) may be injected into the envelope enclosure through the filling port, followed by heat-sealing both the vent opening and the filling port. Alternatively the envelope may be filled to a given level, and the ports used to increase or decrease the amount of fluid filling material.

The size and shape of the envelope may vary over wide ranges. It is contemplated that width may be from 2 inches or more to as wide as 12 inches with 5 to 7 inches being the preferred range for the width. It is preferred that the lateral portions of the pad extend under the person using the pad so that the weight of the person will tend to cause the flowable fluid to flow toward the central region of the pad. The pad must be arranged in such a manner that the upper surface of the envelope can move upwardly when flowable fluid is thrust to the center of the pad. To this extent, a relatively firm supporting surface beneath the pad is required in order to cause the fluid to flow upwardly.

The hemorrhoid pad may be secured to the seating area described above, through the use of anchors made from a hook and loop-type fastner, such as those sold under the name of "Velcro" or by gluing, in order to provide a permanent implacement. However, as is mentioned above, the pad may be used without a permanent cushion member and may, upon occasion, be inserted in articles of clothing.

The Fluid Filling Material

The quantity of filling fluid placed in the pad will vary depending upon the shape of the pad. It is considered important that the pad be partially filled, thus leaving space for the flowable fluid to flow within the pad and deform the pad without rupture. It is essential that the amount of flowable fluid selected fill up the space beneath the anus of a seated person, but it is preferred that the fluid extend laterally beyond the space beneath the anus, so that the weight of the seated person causes the flowable material in lateral portions 12 of the pad to flow inwardly. The inward flow, when combined with the supporting surface, produces the upward supporting pressure which is necessary to support the hemorrhoid and provide relief from the pain thereof.

In its broadest aspect, the present invention contemplates use of any flowable material to fill the pad, as described above. The flowable material may be selected from a number of different fluid types. Gases, such as air may be used, but liquids such as water are preferable because the weight of the water provides more stability and a better anchor for the pad. However, it is preferred to employ as the fluid a highly viscous liquid, i.e., plastic or viscous thixotropic material, which flows gradually when pressure is applied to it, but which maintains its shape and position in the absence of pressure (hereinafter sometimes referred to as "plastic"). One such viscous fluid is commercially available under the trade name FLO-LITE, the registered trademark of Alden Laboratories. Suitable flowable materials are described and claimed in the U.S. Pat. Nos. listed below, which are incorporated by reference herein:

3,237,319
3,402,411
3,635,849
3,798,799
4,038,762
4,083,127
4,108,928
4,144,658
4,229,546
4,243,754
4,255,202

Additionally, the flowable fitting material described in Applicant's patent application Ser. No. 017,711 filed Feb. 24, 1987, now U.S. Pat. No. 4,728,551, may be used as the flowable material in the practice of the present invention.

The following examples will serve to illustrate hemorrhoid pads of the present invention and provide an understanding of how the invention functions, but it is understood that these examples are set forth for illustrative purposes and that many variations thereon may be made.

EXAMPLES

Example 1

A hemorrhoid pad of the shape illustrated in the drawings is made up using 5 mil polyurethane film and heat sealing the periphery. As is shown by the drawings, the pad is approximately bell-shaped and is $6\frac{1}{4}$ inches wide and $6\frac{3}{4}$ inches long. It is filled with 95 cc of FLO-LITE flowable fluid.

The pad was placed on a wooden chair and a 150 pound man was seated thereon. Using a Basal sphygmomanometer, the pressure on the anal area above the measured blood approximately 60 millimeters of mercury. The capillary pressure in the area of the anus is reported to be about 40 millimeters of mercury in pressure. Thus, the hemorrhoid pad of the present invention provided a net positive pressure of about 20 mil, i.e., the positive pressure in excess of that necessary to match the capillary blood pressure in the blood vessels of the anus area. The hemorrhoid pad provided comfort to the user and dramatically reduced the pain of the hemorrhoids.

Example 2

A hemorrhoid pad similar to that described in Example 1, but filled with 190 cc of flowable fluid is subjected to the same test as in Example 1. While the pad did provide some relief from the pain of hemorrhoids, the tester considered the pressure undesirably high and not as comfortable as the pad tested in Example 1. The pad of Example 2 increased the pressure in the anal area to about 75 millimeters of mercury, i.e., an excess pressure of 35 millimeters of mercury.

It is the object of the invention to provide supporting pressure to the area of the anus and the area of the hemorrhoids. It is believed that supporting pressure somewhat higher than the capillary blood pressure provides the best results, so long as the excess pressure is not so high as to cause pain. Accordingly, the volume of flowable fluid placed within the envelope is variable, depending upon the size and shape of the envelope, the surface on which the envelope will be used, and the size and shape of the person who is to use the hemorrhoid pad.

The capillary blood pressure in the area of the anus has been measured as approximately 40 millimeters of mercury when a person is in a supine position. However, when sitting the actual pressure is increased. It is theorized that the pressure on the capillaries in the area of the anus while sitting could be as high as 60 mil of mercury. It has been found that when the hemorrhoid pads of the present invention are able to provide an upward pressure of 60 mil (approximately equal to the pressure provided by the hemorrhoid pad illustrated in Example 1), that good relief from the hemorhold pain is provided. It is theorized that the pad should provide an upward pressure sufficient to compensate for the blood pressure in the vessels which make up the hemorrhoids. In this way, swelling can be gradually minimized. A slight over-pressure caused by the hemorrhoid pad should, in theory, tend to push the hemorrhoids upwardly and thus provide gentle support for the hemorrhoids. This allows the body's natural healing processes to take place and to accelerate the healing process of the hemorrhoids.

The scope of the invention herein shown and described is to be considered only as illustrative. It will be apparent to those skilled in the art that numerous modifications may be made therein without departure from the spirit of the invention and the scope of the appended claims.

I claim:

1. A portable hemorrhoid supporting cushion assembly comprising a supporting surface, said cushion assembly adapted to be removably positioned on a generally horizontal surface that is adapted to support a seated person, said cushion assembly further comprising a pad comprising:

an envelope comprising an upper, generally smooth, generally continous and generally planar layer and a lower layer, said upper layer comprising a flexible material, said envelope being partially filled with a flowable non-gaseous fluid;

said envelope being positioned on said supporting surface, said supporting surface adapted to support a seated person and to support said pad;

said envelope being no greater in width than 7 inches, said envelope adapted to be positioned under said seated person with portions of said envelope extending at least partially beneath the ischia of said seated person, but not substantially beyond said ischia, whereby the weight of said seated person in combination with said supporting surface, causes fluid within said envelope to move inwardly toward the central longitudinal axis of said envelope and upwardly, thus providing uniform upward hemorrhoid supporting pressure greaer than 40 millimeters of mercury to the anal area of said person.

2. A hemorrhoid supporting assembly as described in claim 1, wherein said envelope is symmetrical about a longitudinal axis.

3. A hemorrhoid supporting assembly as described in claim 1, wherein the upward supporting pressure approximates the blood pressure in the capillaries in the area of the anus.

4. A hemorrhoid supporting assembly as described in claim 1, wherein the upward supporting pressure is about 60 millimeters of mercury.

5. A hemorrhoid supporting assembly as described in claim 1, wherein the volume of the flowable fluid is selected to provide the desired upward supporting pressure.

6. A hemorrhoid supporting assembly as described in claim 5, wherein the volume of flowable fluid is selected to provide an upward supporting pressure of approximately 60 millimeters of mercury.

7. A hemorrhoid supporting assembly as described in claim 1, wherein the fluid is a liquid.

8. A hemorrhoid supporting assembly as described in claim 1, wherein the fluid is plastic.

* * * * *